United States Patent [19]

Chae et al.

[11] Patent Number: 5,654,205
[45] Date of Patent: Aug. 5, 1997

[54] APPARATUS AND METHOD FOR DEPOSITING PARTICLES ONTO A WAFER

[75] Inventors: Seung-ki Chae; Byung-seol Ahn; Sang-kyu Hahm; Jong-soo Kim, all of Kyungki-do, Rep. of Korea

[73] Assignee: Samsung Electronics Co., Ltd., Duwon, Rep. of Korea

[21] Appl. No.: 476,113

[22] Filed: Jun. 7, 1995

[30] Foreign Application Priority Data

May 4, 1995 [KR] Rep. of Korea ............... 95-11019

[51] Int. Cl.⁶ ............... H01L 21/66; G01N 37/00; G01N 15/00; G01B 15/02
[52] U.S. Cl. ............... 438/14; 356/335; 73/28.01; 73/865.5; 438/16
[58] Field of Search ............... 437/8; 55/270; 73/28.01, 28.04, 28.05, 865.5; 356/37, 335, 336

[56] References Cited

U.S. PATENT DOCUMENTS

| | | | |
|---|---|---|---|
| 5,231,865 | 8/1993 | McDermott et al. | 73/28.04 |
| 5,278,626 | 1/1994 | Poole et al. | 356/37 |
| 5,374,396 | 12/1994 | Blackford et al. | 356/335 |

*Primary Examiner*—John Niebling
*Assistant Examiner*—Brian K. Dutton
*Attorney, Agent, or Firm*—Cushman Darby & Cushman, IP Group of Pillsbury Madison & Sutro LLP

[57] ABSTRACT

An apparatus for depositing particles onto a wafer comprises a particle generating means; particle size controlling means connected to an output terminal of the particle generating means; a first transmitting tube connected to an output of the particle size controlling means; second and a third transmitting means connected to an output terminal of the first transmitting tube; first counting means connected to an output terminal of the second transmitting tube; particle depositing means connected to an output terminal of the third transmitting means; second counting means connected to the particle depositing means; and a power supplier connected to the particle depositing means. The apparatus and a method for depositing the particles onto the wafer provide a wafer on which particles of known size and kind are deposited. Also, the particles of a different kind and size are deposited on the same wafer.

14 Claims, 2 Drawing Sheets

APPARATUS AND METHOD FOR DEPOSITING PARTICLES ONTO A WAFER

BACKGROUND OF THE INVENTION

The present invention relates to an apparatus and a method for semiconductor, and more particularly, to an apparatus and a method for depositing particles onto a wafer used for measuring a reliability of an apparatus for examining particle contamination on a wafer.

In manufacturing a semiconductor, inspection processes should be carried out on many items in order to manufacture a final good die. Of many items to be inspected, particles contaminating wafers are principle factor causing electrical open or short at the moment the particles are deposited on the substrate of the semiconductor circuit. For this reason, the processes for inspecting and analyzing the particles are the most important of the every process for manufacturing the semiconductor. That is, it is important to inspect and analyze the particles on a wafer by using the particle inspection and analysis system, thereby preventing contamination of the device by the particles.

Currently, the particles inspection and analysis system (e.g. wafer surface scanner and scanning electron microscope) is applied to a wafer on which the particles of known kind, size and number are deposited to investigate the size and numbers of the particles. When the investigation results are same as the known size and number, the system is considered to have accuracy.

In conventional method, the wafer, on which the polystyrene latex is deposited, is frequently used as a wafer available for measuring the accuracy of the particles inspection and analysis system. And the wafer, on which the polystyrene latex of an uniform size is deposited, is commercially available from VLSI, or manufactured by using the wafer spinner.

FIG. 1 is a diagram roughly showing a conventional apparatus for depositing particles onto a wafer.

The conventional apparatus for depositing particles onto a wafer comprises: an atomizer generating the polystyrene latex; a dryer for drying the polystyrene latex; a differential mobility analyzer (hereinafter, referred to as DMA) discharging only the polystyrene latex of an uniform size after classifying the polystyrene latex by sizes; an impactor passing though only the polystyrene latex of a small size among the discharged polystyrene latex from the DMA; a chamber in which a tube for depositing the polystyrene latex from the impactor onto the wafer is installed; and a counter for counting the number of the lost polystyrene latex not deposited.

The size of the polystyrene latex deposited onto the wafer is controlled by using the DMA.

However, there are disadvantages as follows.

First, the polystyrene latex can be guaranteed for its size due to an uniform size distribution. However it is very difficult to investigate the number of the deposited particles. Therefore, it is difficult to measure the accuracy of the particle inspection and analysis system because, though, the size of the particles can be controlled, the number thereof can not.

Second, many different wafers must be prepared depending on desired particles' kind and size because only the particles of same kind and size can be deposited onto a wafer.

Third, it is difficult to obtain the particles of an uniform size when, besides polystyrene latex, other particles generated during the manufacturing process of the semiconductor are applied to the conventional apparatus.

SUMMARY OF THE INVENTION

An object of the present invention is to provide an apparatus for depositing particles onto a wafer which can control not only the size of the particles but also the number thereof.

Another object of the present invention is to provide an apparatus for depositing particles onto a wafer which can deposit particles of a different kind and size on a wafer.

Still another object of the present invention is to provide a method for depositing particles onto a wafer.

To achieve the above and other objects, the apparatus for depositing the particles onto a wafer according to the present invention comprises: means for generating particles; means for controlling the size of particles connected to an output terminal of the particle generating means; a first transmitting tube connected to an output terminal of means for controlling the size of particles, a second and a third transmitting tubes connected to an output terminal of the first transmitting tube; a first counting means connected to an output terminal of the second transmitting tube; means for depositing particles connected to an output terminal of the third transmitting tube; a second counting means connected to the particle depositing means; and power supplier means connected to the particle depositing means.

In the apparatus for depositing the particles according to the present invention, it is preferable to further comprise a multiplexer connected to an output terminals of the first and second counting means and a computer connected to an output terminal of the multiplexer.

In the depositing apparatus of the present invention, it is preferable that the particle generating means includes: an particle atomizer; an impactor connected to an output terminal of the particle atomizer; heating and cooling unit connected to an output terminal of the impactor; and neutralizer connected to an output terminal of the heating and cooling unit.

And, to achieve the above objects of the present invention, there is provided a method for depositing surface particles comprising the steps of: (a) generating particles; (b) classifying the particles by sizes to select the particles of a desired size; (c) transmitting the selected particles to a first transmitting tube; (d) distributing the particles transmitted to the first transmitting tube to a second and a third transmitting tubes; (e) counting the particles transmitted to the second transmitting tube with the first counting means, at the same time, transmitting the particles transmitted to the third transmitting tube to means for depositing particles; and (f) depositing the particles transmitted to the particle depositing means onto the wafer, at the same time, counting the lost articles not deposited onto the wafer with the second counting means.

It is preferable that the particles are polystyrene latex, dioxysilicon ($SiO_2$), nitride or aluminum (Al).

It is preferable that step (a) is performed in order of: atomizing the particles by using the atomizer; sieving the particles of a large size though the impactor; drying the sieved particles; and neutralizing the dried particles.

It is preferable that step (b) is performed in order of: applying voltage to the means for controlling the size of the particles and selecting only the particles of a size corresponding to the applied voltage.

It is preferable that the number of the particles transmitted to the second transmitting tube and the number of the particles transmitted to the third transmitting tube are the same.

It is preferable that step (e) further comprises the step of counting the number of the particles transmitted to the third transmitting tube with the second counting means.

It is preferable that the particles deposited onto the wafer form a circle centering to at a site where the power supplier is connected to the wafer, and more preferable that the diameter of the circle depends on the applied voltage.

It is preferable that at least one kind of particles are generated in step (a) and the particles of different kinds are applied to step (b) in order depending on their kinds. Also, it is more preferable that particles of different sizes are deposited onto different sites on the same wafer.

It is preferable that at least one size of particles are generated in step (a) and particles of different sizes are applied to step (b) in order depending on their sizes. Also, it is more preferable that particles of different sizes are deposited onto the different sites on the same wafer.

Therefore, it is possible to control not only the size but also the number of the particles. And also, the particles of a different size and kind can be deposited together on the same wafer.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE INVENTION

Figure 1:
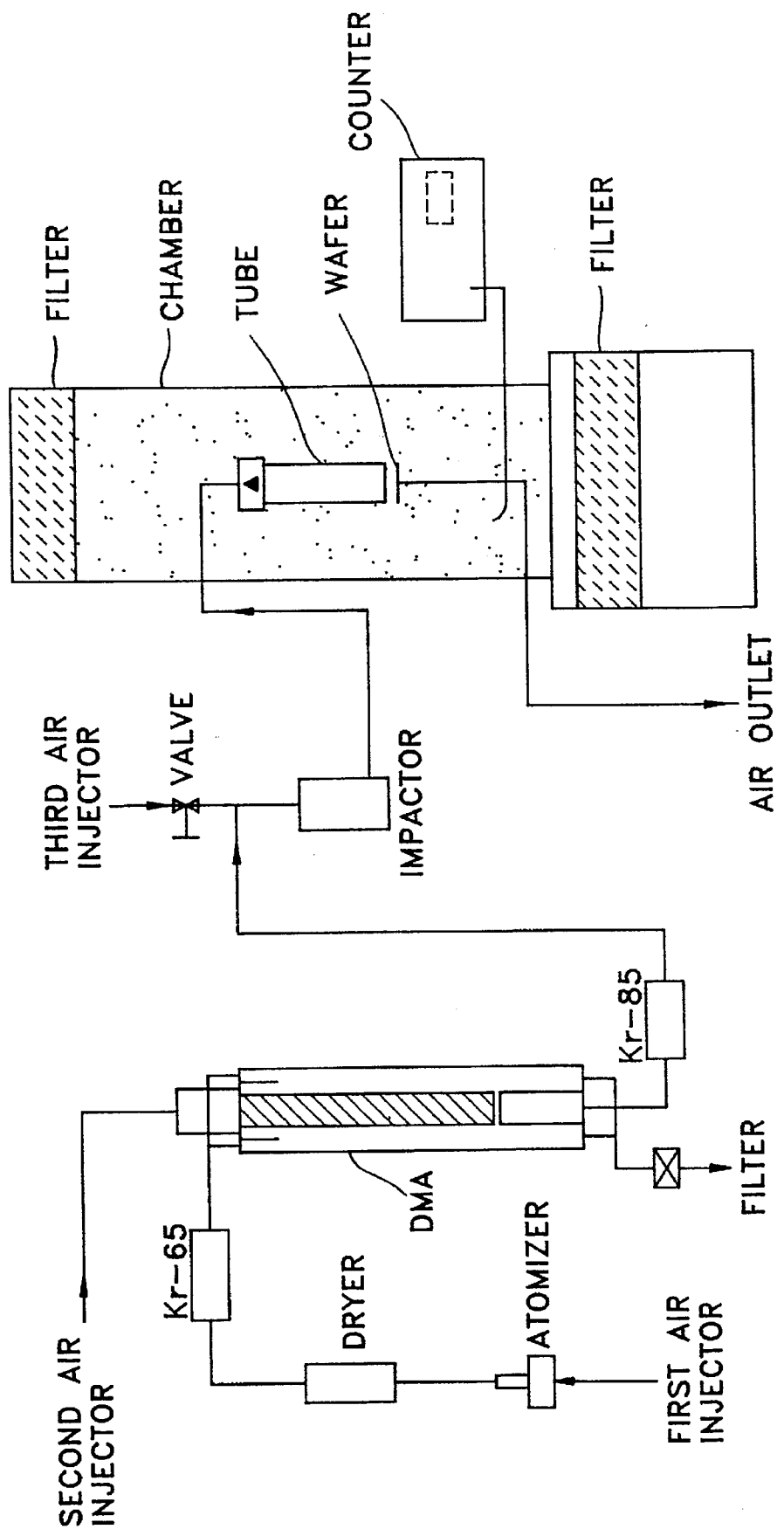
FIG. 1 is a diagram roughly showing a conventional apparatus for depositing particles onto a wafer.
Figure 2:
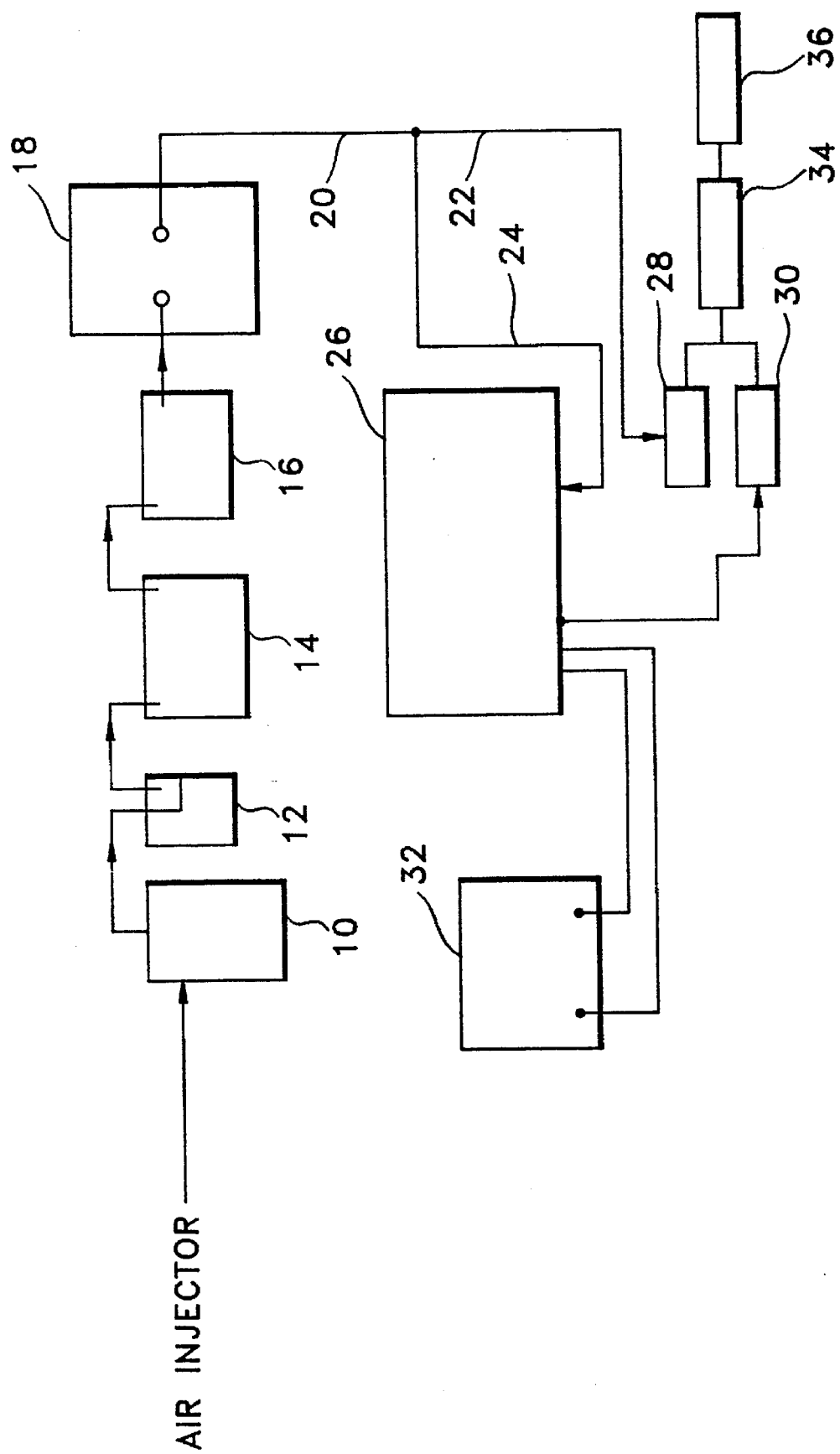
FIG. 2 is a diagram of an apparatus for depositing particles onto a wafer according to the present invention.

Referring to the attached drawings, the present invention will be described in detail.
[Deposition Apparatus]
FIG. 2 is a diagram roughly showing an apparatus for depositing particles onto a wafer according to the present invention.

In FIG. 2, the reference numerals 10 denotes an atomizer, 12 denotes an impactor, 14 denotes a heater and cooler, 16 denotes a neutralizer, 18 denotes a differential mobility analyzer (DMA), 20 denotes a first transmitting tube, 22 denotes a second transmitting tube, 24 denotes a third transmitting tube, 26 denotes a deposition chamber, 28 denotes a first counter, 30 denotes a second counter, 32 denotes a power supplier, 34 denotes a multiplexer, and 36 denotes a computer.

The apparatus for depositing particles onto a wafer includes means for generating particles, means for controlling the size of the particles, a transmitting tube, a counter, means for depositing particles and power supplier means.
(1) particle generating means The particle generating means includes atomizer 10 of which an input terminal is connected to an air injector, impactor 12 of which an input terminal is connected to an output of the atomizer, heater and cooler 14 of which an input terminal is connected to an output of the impactor 12, and neutralizer 16 of which an input terminal is connected to an output terminal of the heater and cooler 14. This means generates particles to be deposited onto the wafer.

In the present invention, besides polystyrene latex, particles generated in the real semiconductor-manufacturing procedure such as dioxysilicon, nitride and aluminum are generated.

(2) means for controlling the size of the particles

The means for controlling the size of particles is composed of DMA 18 of which an input terminal is connected to an output terminal of neutralizer 16 and an output terminal is connected to first transmitting tube 20.

When predetermined voltage is provided to DMA 18, only the particles corresponding to the provided voltage are transmitted to the first transmitting tube through the output terminal of the DMA, thereby transmitting only the particles of a desired size to the first transmitting tube.

Therefore, the particles of a desired size are obtained by controlling the voltage provided to DMA 18.
(3) transmitting tubes The transmitting tubes are composed of: first transmitting tube 20 of which one terminal is connected to the output of DMA 18 and the other terminal is connected to the input terminal of second and third transmitting tube (22 and 24, respectively); second transmitting tube 22 of which one terminal is connected to first transmitting tube 20 and the other terminal is connected to first counter 28; and third transmitting tube 24 of which one terminal is connected to first transmitting tube 20 and the other terminal is connected to deposition chamber 26.

The particles evacuated from DMA 18 to first transmitting tube 20 are transmitted second and third transmitting tubes 22 and 24 respectively, for example, by the ratio of 1:1.
(4) counting means The counting means is composed of first counter 28 of which an input terminal is connected to the output of first transmitting tube 20, and second counter 30 of which an input terminal is connected to deposition chamber 26.

First counter 28 counts the number of the particles transmitted to second transmitting tube 22, which is the same as the number of the particles transmitted to the deposition chamber in the case of the ratio of 1:1, and second counter 30 counts the number of the lost particles not deposited onto the wafer mounted in the deposition chamber.

Therefore, the numbers counted at the first and the second counter are compared, thereby investigating the number of the particles deposited onto the wafer.
(5) particle deposition means The particle deposition means, in which a device for mounting a wafer (not shown) is positioned, is composed of deposition chamber 26 connected to second counter 30 and power supplier 32.

Power supplier 32 is connected to the device for mounting a wafer, thereby making the particles deposited onto the wafer form a circle centering around the site connected to the power supplier 32. A diameter of the circle is adjusted by the voltage provided from the power supplier 32. A site of the particles to be deposited is also adjusted by varying the site connected to the power supplier.

Therefore, the particles of a different size and kind can be deposited on the different site of the same wafer.
(6) power supplier means The power supplier means is connected to deposition chamber 26, thereby adjusting the deposition shape and the deposition site of the particles to be deposited onto the wafer.

First and second counters 28 and 30 are connected to multiplexer 34 and the multiplexer is connected to the computer 36, thereby comparing the numbers counted at the first and the second counters.
[Deposition Method]

Referring to a device for depositing the particles onto a wafer shown in FIG. 2, a method for depositing particles onto a wafer according to the present invention will be described.

The method for depositing particles onto a wafer comprises steps of: (a) generating particles; (b) classifying the particles by sizes; (c) transmitting the particles to the deposition chamber, at the same time, counting the number of the transmitted particles; and (d) depositing the particles onto the wafer, at the same time, counting the number of the lost particles.

[First Embodiment]

Through the air injector, clean air was injected to atomizer 10, from which the particles such as polystyrene latex, dioxysilicon, nitride or aluminum are generated.

The generated particles were transmitted to impactor 12, and then classified by sizes. The particles of a large size hit the impactor plate to fall down and only the particles of a small size were transmitted to heater and cooler 14.

The particles transmitted to heater and cooler 14 contained humidity of less than 10% by heating and cooling, which were then transmitted to neutralizer 16.

The particles transmitted to neutralizer 16 were electrically neutralized and then transmitted to DMA 18.

When predetermined voltage was applied to DMA 18, only the particles of the size corresponding to the applied voltage were transmitted to the output terminal of the DMA. In general, the higher the voltage was, the bigger was the size of the particles transmitted to the output terminal thereof.

The particles transmitted to the output terminal of DMA 18 were transmitted to second and third transmitting tubes 22 and 24 via first transmitting tube 20. In the present invention, the numbers of the particles transmitted to the second and third transmitting tubes were the same. That is, when the number of the particles transmitted to first transmitting tube 20 was one hundred, the numbers of the particles transmitted to second and third transmitting tubes 22 and 24 were fifty, respectively.

The number of the particles transmitted to second transmitting tube 22 was counted with first counter 28, for example, using computer numerical control.

The particles transmitted to third transmitting tube 24 were transmitted to deposition chamber 26, and thereafter deposited onto the wafer (not shown). Of the particles transmitted to the deposition chamber, the lost particles not deposited onto the wafer were counted with second counter 30, thereby investigating the accurate number of the particles deposited onto the wafer. That is, when the number of the particles counted with the first counter was 50 and the number counted with the second was 0, the particle deposited onto the wafer was found to be 50.

On the other hands, the deposition site and the deposition shape of the particles transmitted to the deposition chamber differed depending on the position where power supplier 32 and the wafer mounting device are connected and on the magnitude of the voltage applied from the power supplier.

The particles were deposited onto the periphery of the wafer in a circle when power supplier 32 was connected to the periphery of the wafer, and they were deposited onto the center of the wafer in a circle when power supplier 32 is connected to the center of the wafer. Also, the higher the voltage provided from the power supplier was, the longer was the diameter of the circle formed by the deposited particles. And, the lower the voltage provided from the power supplier was, the shorter was the diameter of the circle formed by the deposited particles.

[Second Embodiment]

While the above first embodiment gives a description of a method for depositing particles of a same kind and size onto the same wafer, the second embodiment 2 explains a method for depositing particles of a different kind on the same wafer.

Prepared the same number of atomizers as the particles' kind, and thereafter generated particles. The generated particles were passed through impactor 12, heater and cooler 14, and neutralizer 16 in order, and then transmitted to DMA 18 to classify the particles by sizes.

Thereafter, repeated the same process as explained in the first embodiment to deposit the particles transmitted to deposition chamber 26 onto the predetermined site of the wafer. The deposition site was determined by adjusting the connection site of the power supplier.

[Third Embodiment]

The third embodiment explains a method for depositing particles of a different size on the same wafer.

The particles generated from atomizer 10 were passed through impactor 12, heater and cooler 14 and neutralizer 16, and then transmitted to DMA 18. Voltages of different level were applied to DMA 18 to classify the particles by sizes, and the classified particles of a different size were then transmitted to the output terminal of DMA 18.

Thereafter, repeated the same process as explained in the first embodiment and the particles transmitted to deposition chamber 26 in order were then deposited onto the predetermined site of the wafer. The site for deposition is determined by adjusting the site where the power supplier is connected.

According to an apparatus and a method for depositing particles onto a wafer of the present invention, a wafer deposited with the particles of known size and number and wafer deposited with the particles of different kinds and sizes can be obtained.

And, the particles discharged from the atomizer are passed through the impactor, heater and cooler, and neutralizer, thereby obtaining desired clean particles.

The present invention is not limited to the above examples and many other variations can be available to those skilled in this art.

What is claimed is:

1. A method for depositing particles onto a wafer comprising the steps of:

(a) generating said particles;

(b) classifying said particles by sizes to select particles of a desired size;

(c) transmitting said selected particles to a first transmitting tube;

(d) distributing said particles transmitted to said first transmitting tube to a second and a third transmitting tubes;

(e) counting said particles transmitted to said second transmitting tube with a first counter, at the same time, transmitting the particles transmitted to said third transmitting tube to a particle depositing means; and depositing the particles transmitted to said particle depositing means, at the same time, counting the lost particles not deposited onto the wafer with a second counter.

2. A method for depositing particles onto a wafer as claimed in claim 1, wherein said particles are polystyrene latex, deoxysilicon, nitride, or aluminum.

3. A method for depositing particles onto a wafer as claimed in claim 1, wherein step (a) is performed in order of: atomizing said particles by using an atomizer; sieving the particles of a large size with an impactor; drying the particles passed through said impactor; and neutralizing the dried particles.

4. A method for depositing particles onto a wafer as claimed in claim 1, wherein step (b) is performed by applying voltage to said means for controlling the size of particles, and then selecting the particles of a size corresponding to said applied voltage.

5. A method for depositing particles onto a wafer as claimed in claim 1, wherein the number of said particles transmitted to said second transmitting tube and the number of said particles transmitted to third transmitting tube are the same.

6. A method for depositing particles onto a wafer as claimed in claim 1, wherein step (e) comprises further steps of counting said particles transmitted to said third transmitting tube by using said second counter.

7. A method for depositing particles onto a wafer as claimed in claim 1, wherein said particles are deposited onto said wafer in a circle centering at a site where a power supplier is connected to said wafer.

8. A method for depositing particles onto a wafer as claimed in claim 7, wherein a diameter of said circle varies according to a voltage applied to said wafer by said power supplier.

9. A method for depositing particles onto a wafer as claimed in claim 1, wherein at least one kind of particles are generated in step (a).

10. A method for depositing particles onto a wafer as claimed in claim 9, wherein said particles are classified by kinds and pass through step (b) in order depending on their kinds.

11. A method depositing particles onto a wafer as claimed in claim 10, wherein the particles classified by kinds are deposited on different sites of said wafer.

12. A method for depositing particles onto a wafer as claimed in claim 11, wherein at least one size of particles are generated in step (a).

13. A method for depositing particles onto a wafer as claimed in claim 12, wherein said particles are classified by sizes and pass through step (b) in order depending on their sizes.

14. A method for depositing particles onto a wafer as claimed in claim 13, wherein the particles classified by sizes are deposited at different sites of wafer depending on their sizes.

* * * * *